US007094884B2

(12) United States Patent
Scholz et al.

(10) Patent No.: US 7,094,884 B2
(45) Date of Patent: Aug. 22, 2006

(54) SOLUBLE COMPLEXES OF AMYLOD β PEPTIDE AND PEPTIDYL PROLYL ISOMERASE CHAPERONE AND METHODS OF MAKING AND USING THEM

(75) Inventors: Christian Scholz, Penzberg (DE); Elke Faatz, Huglfing (DE); Peter Schaarschmidt, Uffing (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 291 days.

(21) Appl. No.: 10/443,654

(22) Filed: May 22, 2003

(65) Prior Publication Data

US 2005/0112720 A1 May 26, 2005

Related U.S. Application Data

(63) Continuation-in-part of application No. 10/179,905, filed on Jun. 24, 2002, which is a continuation-in-part of application No. 10/167,774, filed on Jun. 10, 2002, now abandoned.

(30) Foreign Application Priority Data

| Jun. 22, 2001 | (EP) | 01115225 |
|---|---|---|
| Aug. 31, 2001 | (EP) | 01120939 |
| Dec. 20, 2001 | (WO) | PCT/EP02/14631 |

(51) Int. Cl.
*A61K 38/24* (2006.01)
*C07K 14/00* (2006.01)

(52) U.S. Cl. ............... 530/399; 530/350; 435/320.1; 536/23.1

(58) Field of Classification Search ............... 530/399, 530/350; 435/320.1; 536/23.1
See application file for complete search history.

(56) References Cited

U.S. PATENT DOCUMENTS

| 4,735,896 A | 4/1988 | Wang et al. |
|---|---|---|
| 4,879,212 A | 11/1989 | Wang et al. |
| 4,945,042 A | 7/1990 | Geiger et al. |
| 6,207,420 B1 | 3/2001 | Harrison et al. |
| 6,316,405 B1 | 11/2001 | Rich et al. |

FOREIGN PATENT DOCUMENTS

| AU | 597884 | 4/1986 |
|---|---|---|
| EP | 0 280 211 B1 | 11/1994 |
| EP | 0 396 559 B1 | 8/1996 |
| EP | 1 077 262 | 2/2001 |
| WO | WO 92/22573 | 12/1992 |
| WO | WO 93/21346 | 10/1993 |
| WO | WO 94/08012 | 4/1994 |
| WO | WO 98/13496 | 4/1998 |
| WO | WO/00/20606 | 4/2000 |
| WO | WO 00/26251 | 5/2000 |

OTHER PUBLICATIONS

Bardwell, J., *Building Bridges: Disulphide Bond Formation in Cell*, Molecular Microbiology (1994) 14(2), 199–205.
Bessinger, M., et al., *How Chaperones Fold Proteins*, Biol. Chem., vol. 379, pp. 245–259, Mar. 1998.
Bothmann, H., et al., *The Periplasmic Escherichia coli Peptidylprolyl cis,trans–Isomerase FkpA*, The Journal of Biological Chemistry, vol. 275, No. 22, Issue of Jun. 2, pp. 17100–17105, 2000.
Braden, B., et al., *Structural Features of the Reactions Between Antibodies and Protein Antigens*, The FASEB Journal, pp. 9–16, vol. 9, Jan. 1995.
Buchner, J., *Supervising The Fold: Functional Principles of Molecular Chaperones*, The FASEB Journal, pp. 10–19, vol. 10, Jan. 1996.
Butler, J.E., et al., *The Physical and Functional Behavior of Capture Antibodies Adsorbed on Polystyrene*, Journal of Immunological Methods, 150 (1992), 77–90.
Caffrey, M., et al., *Biophysical Characterization of gp41 Aggregates Suggests a Model for the Molecular Mechanism of HIV–Associated Neurological Damage and Dementia*, The Journal of Biological Chemist, vol. 275, No. 26, Issue of Jun. 30, pp. 19877–19882, 2000.
Chan, D., et al., *Core Structure of gp41 From The HIV Envelope Glycoprotein*, Cell, vol., 89, 263–273, Apr. 18, 1997.
Crooke, E., et al., *Trigger Factor: A Soluble Protein That Folds Pro–OmpA Into A Membrane–Assembly–Competent Form*, Biochemistry, vol. 84, pp. 5216–5220, Aug. 1987.
Danese, P., et al., *The Cpx Two–Component Signal Transduction Pathway of Escherichia coli Regulates Transcription of the Gene Specifying the Stress–Inducible Periplasmic Protease, DegP*, Genes & Development, pp. 387–398 (1995).
Dartigalongue, C., et al., *A New Heat–Shock Gene, ppiD, Encodes A Peptidyl–Prolyl Isomerase Required For Foling of Other Membrane Proteins in Escherichia Coli*, The EMBO Journal, vol. 17, No. 14, pp. 3968–2980, 1998.
Dent, A., et al., *The Preparation of Protein—Protein Conjugates, Heterobifunctional Reagents Based on the Biotin–Avidin Interaction*, Chapter 5, pp. 261–263.
Doms, R., et al., *HIV–1 Membrane Fusion: Targets of Opportunity*, The Journal of Cell Biology, pp. F9–F13, vol. 151, No. 2, Oct. 16, 2000.
Egan, D.A., et al., *Equilibruim Denaturation of Recombinant Human FK Binding Protein in Urea*, Biochemistry, pp. 1920–1927, vol. 32, No. 8, 1993.

(Continued)

*Primary Examiner*—Karen Cochrane Carlson
(74) *Attorney, Agent, or Firm*—Brinks Hofer Gilson & Lione

(57) ABSTRACT

The present invention relates to the diagnosis of Alzheimer's Disease. It especially teaches the production of a soluble Aβ-chaperone complex and the advantageous use of such chaperone-Aβ complex, especially in the detection of Aβ in an immunoassay, as well as its use as an immunogen.

53 Claims, 2 Drawing Sheets

OTHER PUBLICATIONS

Ehrnsperger, Monika, et al., *Stabilization of Proteins and Peptides in Diagnostic Immunological Assays by the Molecular Chaperone Hsp25*, Analytical Biochemistry 259 (1998), pp. 218–225.

Endrich, et al., *The V3 Loop of a Human Immunodeficiency Virus Type–1 Envelope Protein is a High–Affinity Ligand for Immunophilins Present in Human Blood*, Eur. J. Biochem., 252–441–446 (1998).

Fischer, G., *Cyclophilin and Peptidyl–Prolyl Cis–Trans Isomerase are Probably Identical Proteins*, Nature, vol. 337 Feb. 2, 1989.

Frech, C., et al. *Preferential Binding of an Unfolded Protein to DsbA*, The EMBO Journal, vol. 15, No. 2, pp. 392–398, 1996.

Gething, M., *Protein Folding in the Cell*, Nature, vol. 355, Jan. 2, 1992.

Goethel, S.F., et al., *Peptide–Proly Cis–Trans Isomerases, a Superfamily of Ubiquitous Folding Catalysts*, Cellular and Molecullar Life Sciences (CMLS), pp. 423–436, vol. 55, 1999.

Guyader, M., et al. *Genome Organization and Transactivation of the Human Immunodeficiency Virus Type 2*, Nature, vol. 326 Apr. 16, 1987.

Hottenrott, S., et al., *The Escherichia Coli SlyD is a Metal–Ion–Regulate Peptidyl–Prolyl Cis/Trans–Isomerase*, The Journal of Biological Chemistry, vol. 272, No. 25, Issue of Jun. 20, pp. 15697–15701, 1997.

Ivery, M.T.G., *Immunophilins: Switched on Protein Binding Domains?* Med Res Rev., Nov. 2000, pp. 452–484.

Kay, J.E., *Structure–Function Relationships in the FK506–Binding Proteing (FKBP) Family of Peptidylprolyl Cis–Trans Isomerases*, Biochem. J., (1996), 314, 361–385.

Kojouharova, M.S., et al., *Differential Binding of IgG and of a HIV gp41 Peptide by the B Chain and A Chain Globular Head Sequences of C1q, Respectively*, Journal of Immunology, 161:4352–4331.

Lane, W.S., *Complete Amino Acid Sequence of the FK506 and Rapamycin Binding Protein, FKBP, Isolated from Calf Thymus*, Journal of Protein Chemistry, pp. 151–160, vol. 10, No. 2, 1991.

Lu, Min., et al., *A Trimeric Structured Domain of the HIV–1 Transmembrane Glycoprotein*, Nature Structural Biology, pp. 1–8, vol. 2, No. 12, Dec. 1995.

Matsubara, Etsuro, et al., *Apolipoprotein J and Alzheimer's Amyloid β Solubility*, Biochem J. 316 (1996), pp. 671–679.

Meister, S., et al., *Basic Amino Acid Residues in the V3 Loop of Simian Immunodificiency Virus Envelope Alter Viral Coreceptor Tropism and Infectivity but Do Not Allow Efficient Utilization of CXCR4 as Entry Cofactor*, Virology, 284, 287–296 (2001).

Missiakas, D., et al., *Identification and Characterization of a New Disulfide Isomerase–Like Protein (DsbD) in Escherichia Coli*, The EMBO Journal, vol. 14, No. 14, pp. 3415–3424, 1995.

Missiakas, D., et al., *New Components of Protein Foling in Extracytoplasmic Compartments of Escherichia Coli SurA, FkpA and Skp/OmpH*, Molecular Microbiology, (1996) 21(4), pp. 871–884.

Otteken, et al. *Calreticulin Interacts With Newly Synthesized Human Immunodeficiency Virus Type 1 Envelope Gylcoprotein, Suggesting A Chaperone Function Similar To That Of Calnexin*, The Journal of Biological Chemistry, vol. 271, No. 1, Jan. 5, 1996, pp. 97–103.

Pennisi, Elizabeth, *Expanding the Eukaryote's Cast of Chaperones*, Science, vol. 274, Dec. 1996 pp. 1613–1614.

Prusiner, S.B., *Prions*, Nobel Lecture, vol. 95, pp. 13363–1383, Nov. 1998.

Rahfeld, J., et al., *Confirmation of the Existence of a Third Family Among Peptidyl–Prolyl Cisltrans Isomerases Amino Acid Sequence and Recombinant Production of Parvulin*, FEBS Letters, 352 (1994) pp. 180–184.

Ramm, K., et al., *The Periplasmic Escherichia Coli Peptidylprolyl Cis, Trans–Isomerase FkpA*, The Journal of Biological Chemistry, vol., 275, No. 22, Issue of Jun. 2, pp. 17106–17113, 2000.

Ratner, L., et al., *Complete Nucleotide Sequence of the AIDS Virus, HTLV–III*, Nature, pp. 277–284, vol. 313–Jan. 24, 1985.

Rool, M.J., et al., *Protein Design of an HIV–1 Entry Inhibitor*, Science, pp. 884–888, vol., 291, Feb. 2, 2001.

Scholz, C., et al., *Cooperation of Enzymatic and Chaperone Functions of Trigger Factor in the Catalysis of Protein Folding*, The EMBO Journal. vol. 16, No. 1, pp. 54–58, 1997.

Scholz, C., *Autocatalytic Folding of the Folding Catalyst FKBP12*, The Journal of Biological Chemistry, vol., 271, No. 22, Issue of May 31, pp. 12703–12707, 1996.

Speth, C., et al., *A 60 kD Heat–Shock Protein–Like Molecular Interacts with the HIV Transmembrane Glycoprotein gp41*, Molecular Immunology, 36 (1999) 619–628.

Stoller, G., et al., A Ribosome–Associated Peptidyl–Prolyl Cis/Trans Isomerase Identified As the Trigger Factor, The EMBO Journal, vol. 14, No. 20, pp. 4939–4948, 1995.

Tijssen, P., *Preparation of Enzyme–Antibody of Other Enzyme–Macromolecule Conjugates*, Practice and Theory of Enzyme Immunoassays, Chapter 11, pp. 221–279, 1985.

Wang, C., et al., *Protein Disulfide Isomerase is Both an Enzyme and a Chaperone*, The FASEB Journal, vol. 7, pp. 1515–1517, Dec. 1993.

Wild, C., et al., *A Synthetic Peptide Inhibitor of Human Immunodeficiency Virus Replication: Correlation Between Solution Structure and Viral Inhibition*, Proc. Natl. Acad. Sci., vol. 89, pp. 10537–10541, Nov. 1992.

Wingfield, P.T., et al., *The Extracellular Domain of Immunodeficiency Virus gp41 Protein: Expression in Escherichia Coli, Purification, and Crystallization*, Protein Science, p. 1653–1660 (1997).

Winter, J., *Increases Production of Human Proinsulin in the Periplasmic Space of Escherichia Coli by Fusion to DsbA*, Journal of Biotechnology, 84 (2000) 175–185.

Yang, Yunning, et al., *Communication The Chaperone BiP/GRP78 Binds to Amyloid Precursor Protein and Decreases Aβ40 and Aβ42 Secretion*, The Journal of Biological Chemistry, vol. 273, No. 40, Oct. 1998, pp. 25552–25555.

Zarnt, T., et al., *Modular Structure on the Trigger Factor Required for High Activity in Protein Funding*, Journal of Molecular Biolology (1997), 271, 827–837.

SEQUENCE LISTING

<160> NUMBER OF SEQ ID NOS: 2

<210> SEQ ID NO 1
<211> LENGTH: 1281
<212> TYPE: DNA
<213> ORGANISM: Artificial Sequence
<220> FEATURE:
<223> OTHER INFORMATION: Nucleic acid sequence coding for a fusion protein
<220> FEATURE:
<221> NAME/KEY: CDS

<222> LOCATION: (4)..(1278)
<223> OTHER INFORMATION:

<400> SEQUENCE: 1

```
cat atg aaa gta gca aaa gac ctg gtg gtc agc ctg gcc tat cag gta         48
    Met Lys Val Ala Lys Asp Leu Val Val Ser Leu Ala Tyr Gln Val
    1               5                   10                  15 cgt aca gaa gac ggt gtg ttg gtt gat gag tct ccg gtg agt gcg ccg         96
Arg Thr Glu Asp Gly Val Leu Val Asp Glu Ser Pro Val Ser Ala Pro
                20                  25                  30 ctg gac tac ctg cat ggt cac ggt tcc ctg atc tct ggc ctg gaa acg        144
Leu Asp Tyr Leu His Gly His Gly Ser Leu Ile Ser Gly Leu Glu Thr
            35                  40                  45 gcg ctg gaa ggt cat gaa gtt ggc gac aaa ttt gat gtc gct gtt ggc        192
Ala Leu Glu Gly His Glu Val Gly Asp Lys Phe Asp Val Ala Val Gly
        50                  55                  60 gcg aac gac gct tac ggt cag tac gac gaa aac ctg gtg caa cgt gtt        240
Ala Asn Asp Ala Tyr Gly Gln Tyr Asp Glu Asn Leu Val Gln Arg Val
65                  70                  75                  80 cct aaa gac gta ttt atg ggc gtt gat gaa ctg cag gta ggt atg cgt        288
Pro Lys Asp Val Phe Met Gly Val Asp Glu Leu Gln Val Gly Met Arg
                85                  90                  95 ttc ctg gct gaa acc gac cag ggt ccg gta ccg gtt gaa atc act gcg        336
Phe Leu Ala Glu Thr Asp Gln Gly Pro Val Pro Val Glu Ile Thr Ala
                100                 105                 110 gtt gaa gac gat cac gtc gtg gtt gat ggt aac cac atg ctg gcc ggt        384
Val Glu Asp Asp His Val Val Val Asp Gly Asn His Met Leu Ala Gly
            115                 120                 125 cag aac ctg aaa ttc aac gtt gaa gtt gtg gcg att cgc gaa gcg act        432
Gln Asn Leu Lys Phe Asn Val Glu Val Val Ala Ile Arg Glu Ala Thr
        130                 135                 140 gaa gaa gaa ctg gct cat ggt cac gtt cac ggc gcg cac gat cac cac        480
Glu Glu Glu Leu Ala His Gly His Val His Gly Ala His Asp His His
145                 150                 155 cac gat cac gac cac gac ggt ggc ggt tcc ggc ggt ggc tct ggt ggc        528
His Asp His Asp His Asp Gly Gly Gly Ser Gly Gly Gly Ser Gly Gly
160                 165                 170                 175 gga agc ggt ggc ggt tcc ggc ggt ggc tct ggt ggc ggt aaa gta gca        576
Gly Ser Gly Gly Gly Ser Gly Gly Gly Ser Gly Gly Gly Lys Val Ala
                180                 185                 190 aaa gac ctg gtg gtc agc ctg gcc tat cag gta cgt aca gaa gac ggt        624
Lys Asp Leu Val Val Ser Leu Ala Tyr Gln Val Arg Thr Glu Asp Gly
            195                 200                 205 gtg ttg gtt gat gag tct ccg gtg agt gcg ccg ctg gac tac ctg cat        672
Val Leu Val Asp Glu Ser Pro Val Ser Ala Pro Leu Asp Tyr Leu His
        210                 215                 220 ggt cac ggt tcc ctg atc tct ggc ctg gaa acg gcg ctg gaa ggt cat        720
Gly His Gly Ser Leu Ile Ser Gly Leu Glu Thr Ala Leu Glu Gly His
225                 230                 235 gaa gtt ggc gac aaa ttt gat gtc gct gtt ggc gcg aac gac gct tac        768
Glu Val Gly Asp Lys Phe Asp Val Ala Val Gly Ala Asn Asp Ala Tyr
240                 245                 250                 255 ggt cag tac gac gaa aac ctg gtg caa cgt gtt cct aaa gac gta ttt        816
Gly Gln Tyr Asp Glu Asn Leu Val Gln Arg Val Pro Lys Asp Val Phe
                260                 265                 270 atg ggc gtt gat gaa ctg cag gta ggt atg cgt ttc ctg gct gaa acc        864
Met Gly Val Asp Glu Leu Gln Val Gly Met Arg Phe Leu Ala Glu Thr
            275                 280                 285 gac cag ggt ccg gta ccg gtt gaa atc act gcg gtt gaa gac gat cac        912
Asp Gln Gly Pro Val Pro Val Glu Ile Thr Ala Val Glu Asp Asp His
```

-continued

```
             290                 295                 300
gtc gtg gtt gat ggt aac cac atg ctg gcc ggt cag aac ctg aaa ttc      960
Val Val Val Asp Gly Asn His Met Leu Ala Gly Gln Asn Leu Lys Phe
            305                 310                 315 aac gtt gaa gtt gtg gcg att cgc gaa gcg act gaa gaa gaa ctg gct     1008
Asn Val Glu Val Val Ala Ile Arg Glu Ala Thr Glu Glu Glu Leu Ala
320                 325                 330                 335 cat ggt cac gtt cac ggc gcg cac gat cac cac gat cac gac cac         1056
His Gly His Val His Gly Ala His Asp His His Asp His Asp His
                340                 345                 350 gac ggt ggc ggt tcc ggc ggt ggc tct ggt ggc gga tcc ggt ggc ggt     1104
Asp Gly Gly Gly Ser Gly Gly Gly Ser Gly Gly Gly Ser Gly Gly Gly
            355                 360                 365 tcc ggc ggt ggc tct ggt ggc ggt gac gct gaa ttc cgt cac gac tcc     1152
Ser Gly Gly Gly Ser Gly Gly Gly Asp Ala Glu Phe Arg His Asp Ser
            370                 375                 380 ggt tac gaa gtt cac cac cag aaa ctg gtt ttc ttc gct gaa gac gtt     1200
Gly Tyr Glu Val His His Gln Lys Leu Val Phe Phe Ala Glu Asp Val
385                 390                 395 ggt tcc aac aaa ggt gct atc atc ggt ctg atg gtt ggt ggt gtt gtt     1248
Gly Ser Asn Lys Gly Ala Ile Ile Gly Leu Met Val Gly Gly Val Val
400                 405                 410                 415 atc gct ctc gag cac cac cac cac cac cac tga                         1281
Ile Ala Leu Glu His His His His His His
                420                 425

<210> SEQ ID NO 2
<211> LENGTH: 425
<212> TYPE: PRT
<213> ORGANISM: Artificial Sequence
<220> FEATURE:
<223> OTHER INFORMATION: Amino acid sequence of a fusion protein

<400> SEQUENCE: 2

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp His Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190
```

```
Asp Leu Val Val Ser Leu Ala Tyr Gln Val Arg Thr Glu Asp Gly Val
            195                 200                 205

Leu Val Asp Glu Ser Pro Val Ser Ala Pro Leu Asp Tyr Leu His Gly
            210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
            275                 280                 285

Gln Gly Pro Val Pro Val Glu Ile Thr Ala Val Glu Asp Asp His Val
            290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His Asp His Asp His His Asp
                340                 345                 350

Gly Gly Gly Ser Gly Gly Gly Ser Gly Gly Gly Ser Gly Gly Gly Ser
            355                 360                 365

Gly Gly Gly Ser Gly Gly Gly Asp Ala Glu Phe Arg His Asp Ser Gly
            370                 375                 380

Tyr Glu Val His His Gln Lys Leu Val Phe Phe Ala Glu Asp Val Gly
385                 390                 395                 400

Ser Asn Lys Gly Ala Ile Ile Gly Leu Met Val Gly Gly Val Val Ile
                405                 410                 415

Ala Leu Glu His His His His His
            420                 425
```

SOLUBLE COMPLEXES OF AMYLOD β PEPTIDE AND PEPTIDYL PROLYL ISOMERASE CHAPERONE AND METHODS OF MAKING AND USING THEM

REFERENCE TO RELATED APPLICATIONS

This application is a continuation-in-part application of Ser. No. 10/179,905, filed Jun. 24, 2002, which is a continuation-in-part application of Ser. No. 10/167,774, filed Jun. 10, 2002, now abandoned, which claims foreign priority to European Patent Applications EP 01115225.3 filed Jun. 22, 2001, and EP 01120939.2, filed Aug. 31, 2001. This application also claims foreign priority to PCT/EP02/14631, filed Dec. 20, 2002. The disclosures of the priority applications are incorporated by reference herein in their entireties.

The present invention relates to the diagnosis of Alzheimer's Disease (AD). It especially teaches the production of a soluble Aβ-chaperone complex and the advantageous use of such chaperone-Aβ complex, especially in the detection of Aβ in an immunoassay, as well as its use as an immunogen.

BACKGROUND

Alzheimer's disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in all races and ethnic groups worldwide and presents a major present and future public health problem.

In Germany about 65,000 cases of AD are newly diagnosed every year. The disease is currently estimated to affect about two to three million individuals in the United States alone. AD is at present incurable. No treatment that effectively prevents AD or reverses its symptoms or course is currently known.

The brains of individuals with AD exhibit characteristic lesions termed senile plaques, and neurofibrillary tangles. Large numbers of these lesions are generally found in several areas of the human brain important for memory and cognitive function in patients with AD. Smaller numbers of these lesions in a more restricted anatomical distribution are sometimes found in the brains of aged humans who do not have clinical AD. Senile plaques and amyloid angiopathy also characterize the brains of individuals beyond a certain age with Trisomy 21 (Down's Syndrome) and Hereditary Cerebral Hemorrhage with Amyloidosis of the Dutch-Type (HCHWA-D).

At present, a definitive diagnosis of AD usually requires observing the aforementioned lesions in the brain tissue of patients who have died with the disease or, rarely, in small biopsied samples of brain tissue taken during an invasive neurosurgical procedure. The principal chemical constituent of the senile plaques and vascular amyloid deposits (amyloid angiopathy) characteristic of AD and the other disorders mentioned above is an approximately 4.2 kilodalton (kD) protein of about 3943 amino acids originally designated the amyloid-β peptide (Aβ) or sometimes βAP, AβP or β/A4. Nowadays the nomenclature Aβ is generally accepted to describe this polypeptide.

Aβ was first purified and a partial amino acid sequence reported in Glenner, G. G., and Wong, C. W., Biochem. Biophys. Res. Commun. 120 (1984) 885–890. The isolation procedure and the sequence data for the first 28 amino acids are described in U.S. Pat. No. 4,666,829. Forms of Aβ having amino acids beyond number 40 were first reported by Kang, J., et al., Nature 325 (1987) 733–736.

Roher, A. E., et al., Proc. Natl. Acad. Sci. USA 90 (1993) 10836–10840 showed that Aβ(142) is the major constituent in neuritic plaques (90%) with significant amounts of isomerized and racemized aspartyl residues. The authors also showed that Aβ(17–42) also predominates in diffuse plaques (70%), while Aβ(1–40) is the major constituent in the meningovascular plaques, comprising 60% of the total Aβ and, in parenchymal vessel deposits Aβ(1–42) represents 75% of the total Aβ.

Iwatsubo, T., et al., Neuron 13 (1994) 45–53 showed that Aβ 42(43)-positive senile plaques are the major species of Aβ in sporadic Aβ brain.

Molecular biological and protein chemical analyses conducted during the last several years have show that Aβ is a small fragment of a much larger precursor protein, referred to as the amyloid precursor protein (AβP), that is normally produced by cells in many tissues of various animals, including humans. Knowledge of the structure of the gene encoding APP has demonstrated that Aβ arises as a peptide fragment that is cleaved from the carboxy-terminal end of APP by a set of enzymes termed α-, β-, and γ-secretases. The precise biochemical mechanism by which the Aβ fragment is cleaved from APP and subsequently deposited as amyloid plaques in the cerebral tissue and in the walls of cerebral and meningeal blood vessels is currently unknown.

Several lines of evidence indicate that progressive cerebral deposition of Aβ plays a seminal role in the pathogenesis of Aβ and can precede cognitive symptoms by years or decades (for review, see Selkoe, D. J., J. Neuropath. and Exp. Neurol. 53 (1994) 438–447; and Selkoe, D. J., Neuron 6 (1991) 487).

Despite the progress, which has been made in understanding the underlying mechanisms of AD, there remains a need to develop methods for use in diagnosis of the disease.

Numerous biochemical electron microscopic and immunochemical studies have reported that Aβ is highly insoluble in physiologic solutions at normal pH. See, for example, Glenner, G. G., and Wong, C. W., Biochem. Biophys. Res. Commun. 122 (1984) 1131–1135; Masters, C. L., et al., Proc. Natl. Acad. Sci. USA 82 (1985) 4245–4249; Selkoe, D. J., et al., J. Neurochem. 46 (1986) 1820–1834.

Furthermore, this insolubility was predicted by and is consistent with the amino acid sequence of Aβ which includes a stretch of hydrophobic amino acids that constitutes part of the region that anchors the parent protein (APP) in the lipid membranes of cells. Hydrophobic, lipid-anchoring proteins such as the Aβ-part of APP are predicted to remain associated with cellular membranes or membrane fragments and thus not to be present in physiologic extracellular fluids. The aforementioned studies and many others have reported the insolubility in physiologic solution of native Aβ purified from AD brain amyloid deposits or of synthetic peptides containing the Aβ sequence. The extraction of Aβ from cerebral amyloid deposits and its subsequent solubilization has required the use of strong, non-physiologic solvents and denaturants.

Physiologic, buffered salt solutions that mimic the extracellular fluids of human tissues have uniformly failed to solubilize Aβ.

Immunoassays in general are performed at physiological pH. Polypeptides soluble at physiological buffer conditions, therefore, are extensively used in various immunoassay methods, such as, e.g., ELISA (enzyme-linked immunosorbent assay), for example in diagnosis of and screening for a certain disease.

Due to its insolubility under physiological buffer conditions, and due to its sticky nature the Aβ peptide is difficult to use in an immunoassay. E.g., in a sandwich assay format Aβ is difficult to handle, because it tends to aggregate or even precipitate. Due to its sticky nature Aβ may also lead to false results caused by unspecific binding.

Although it is possible to solubilize Aβ by means of strongly chaotropic reagents or appropriate detergents, the material solubilized in such a manner is of limited use as a diagnostic tool.

The insolubility of Aβ at physiological buffer conditions in addition renders this protein a very difficult target of routine (bio-) chemical procedures. The vast majority of "labeling chemistries", i.e., the chemical procedures used for binding a label, e.g., a marker group to a polypeptide, is based on nucleophilic chemistry and thus rather restricted to a pH window from about pH 6 to about pH 8 and thus only works at more or less physiological buffer conditions. These routine procedures, e.g., as described in Aslam, M. and Dent, A., The preparation of protein—protein conjugates in "Bioconjugation", eds. M. Aslam and A. Dent, McMillan Reference, London (1998), pp. 216–363, either do not work properly or are difficult to carry out with the Aβ peptide.

Therefore a tremendous need exists to provide Aβ in a readily soluble form, a form in which Aβ is, e.g., soluble at physiological pH, stable in solution and/or convenient to produce and/or handle.

It was the task of the present invention to investigate whether Aβ can be provided in a form, which is readily soluble at physiological buffer conditions.

We found that folding helpers, e.g., many members of the peptidyl prolyl isomerase (PPI) class, especially from the FKBP family, not only exhibit catalytic activity, but also bring about drastic beneficial effects on solubility of amyloidogenic proteins, or more generally speaking, of proteins tending to aggregation, like the Aβ peptide. They do so by forming soluble complexes with such proteins that are otherwise (i.e. in an unchaperoned, isolated form) prone to aggregation. Aβ which is hardly soluble or insoluble under physiological conditions turned out to be soluble under mild physiological conditions (i.e. without need for solubilizing additives such as detergents or chaotropic agents) once it is present in form of a complex with an appropriate PPI chaperone. Thus, we were able to produce, for example, soluble Aβ-chaperone complexes comprising, e.g., the Aβ(1-42) peptide (otherwise an aggregation prone) protein and SlyD, FkpA or other FKBPs as solubility-conferring chaperones.

A soluble complex comprising an Aβ peptide and a PPI-class chaperone can for example be obtained from a single recombinant protein comprising both an Aβ peptide and a PPI class chaperone. A recombinant protein comprising Aβ and a chaperone selected from the peptidyl-prolyl-isomerase class of chaperones is described.

Most intriguingly, a fusion protein comprising both an Aβ peptide and a PPI chaperone can be solubilized and renatured easily and has been found to form a soluble intramolecular Aβ-chaperone complex that enables e.g., the convenient labeling of said complex.

It is now possible to provide an Aβ in a readily soluble form for use as standard material in immunoassays. It is also possible to produce a labeled chaperone-Aβ complex wherein solely the chaperone is labeled, making sure that the Aβ-antigen is not modified or negatively influenced (e.g. in terms of conformation) by such labeling.

The Aβ-chaperone complexes we describe here provide a convenient means to produce a soluble labeled Aβ peptide for immunoassays irrespective of the detection format used.

The novel complexes comprising Aβ and SlyD, for example, are readily soluble, e.g., under physiological conditions, they can be easily labeled in convenient pH ranges, and they can be used to great advantage in the detection of Aβ by immunological techniques or for immunization.

The Aβ chaperone complex eluted from a Ni-NTA (nickel-nitrilo-triacetate) column at an imidazole concentration of around 150 mM in a buffer of 50 mM sodium phosphate pH 7.8 and 100 mM sodium chloride. The UV-spectrum was monitored at a protein concentration of 36 μM. The shape of the spectrum (especially in the wavelength region >300 nm) highlights the remarkable solubility of the "chaperoned" Alzheimer's Aβpeptide. Stray light effects which would indicate aggregation or association phenomena are not observed. Obviously, the chaperone carrier SlyD—SlyD (=SS) confers an exceptional solubility on the otherwise aggregation-prone peptide Aβ(1-42).

Figure 2:
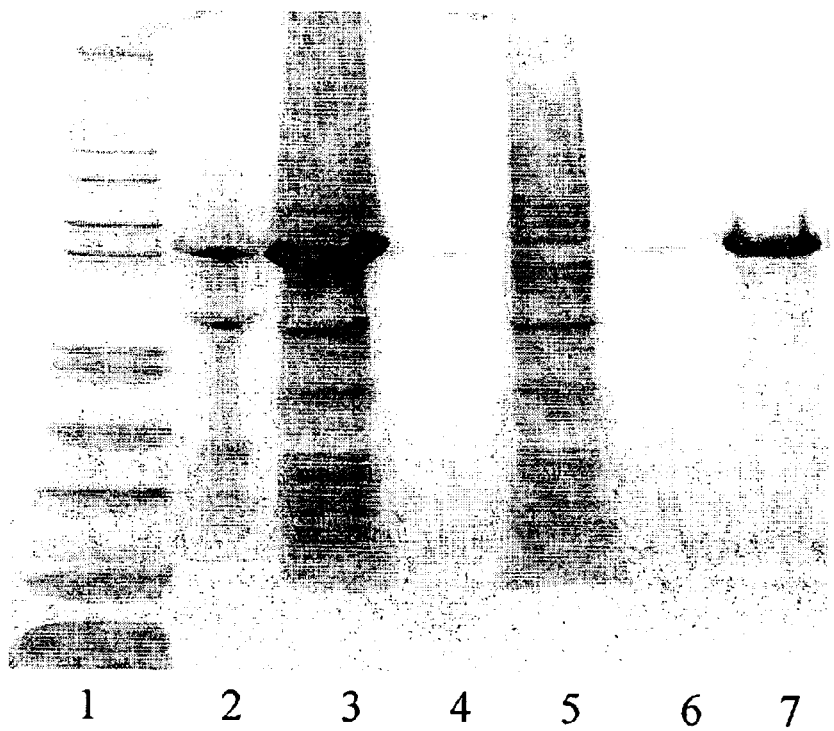

FIG. 2: Purification of SS-Aβ(1-42) as documented by SDS-PAGE. SS-Aβ(1-42) as obtained by matrix-assisted refolding was analyzed by SDS-PAGE. Samples shown are: protein standard M12 from Novagen (lane 1), insoluble fraction after chaotropic lysis (lane 2), soluble fraction after chaotropic lysis (lane 3), Ni-NTA-flowthrough (lane 5), elution pool comprising SS-Aβ(1-42) after matrix-assisted refolding (lane 7). In lanes 4 and 6 no samples has been applied. The gel indicates that the recombinantly produced soluble SS-Aβ(1-42) is available (in surprisingly high purity of >90%) by a simple one-step renaturation/purification protocol.

DETAILED DESCRIPTION

The present invention relates to a method of producing a soluble Aβ-chaperone complex comprising covalently linked an Aβ and a PPI chaperone, comprising: solubilizing said polypeptide, and adjusting the buffer to physiological conditions, wherein the Aβ-chaperone complex formed is soluble to at least 100 nM as measured in a solution which has a pH of 7.4 and consists of 20 mM sodium phosphate and 150 mM sodium chloride.

An Aβ peptide or "Aβ" according to the present invention may be any fragment of the APP of at least 20 contiguous amino acids in length comprising the C-terminal end of the Aβ molecule terminating at amino acid position 38, 39, 40, 41, 42, or 43 of Aβ. More preferred the Aβ peptide is at least 30 amino acids long. Preferably the Aβ is a full-length Aβ starting at amino acid one and ending at the C-terminus of Aβ. Preferred C-termini are peptides ending with Aβ-residues 40, 42 or 43, respectively. Especially preferred are Aβ forms comprising the amino acids from amino acid 1 to amino acid 42 of Aβ(=Aβ(1-42)) and Aβ from amino acid 1 to amino acid 43 of Aβ(=Aβ(1-43)).

In the following Aβ is sometimes also referred to as "target protein".

It is obvious to the skilled artisan that Aβ from non-human other mammalian species, as well as naturally occurring or synthetically produced variants of Aβ may also be used with great advantage and shall also be encompassed by the present invention. The use of human Aβ and naturally occurring variants thereof is most preferred.

A protein is considered "essentially insoluble" if in a buffer consisting of 20 mM sodium-phosphate pH 7.4, 150 mM NaCl it is soluble in a concentration of 50 nM or less. Aβ is essentially insoluble in such buffer and forms aggregates and/or precipitates.

The Aβ-chaperone complex according to the present invention, however, is "soluble" in a buffer consisting of 20 mM sodium phosphate pH 7.4, 150 mM NaCl. In such buffer the target protein Aβ, as comprised in the Aβ-PPI-chaperone complex, is soluble in a concentration of 100 nM or more.

The term "complex" is used to indicate that the peptide domain corresponding to Aβ and the peptide domain corresponding to the chaperone interact with each other whereby the chaperone confers a solubilizing effect to the Aβ.

Production of the soluble chaperone-target protein complex starts from a solubilizing buffer condition, i.e. from a buffer wherein both, the target protein and the chaperone are soluble. An appropriate buffer, which may be termed "non-physiological" or "solubilizing" buffer, has to meet the requirement that both the target protein and the PPI chaperone are not denatured or at least not irreversibly denatured. Starting from such buffer conditions, the chaperone binds to the target protein, and a change of the buffer conditions from non-physiological to physiological conditions is possible without precipitation of the target protein.

An appropriate (non-physiological) buffer, i.e., a buffer wherein both the target protein and the PPI-chaperone are soluble either makes use of high or low pH, or of a high chaotropic salt concentration or of a combination thereof.

Although a chaperone and an Aβ peptide can be used as separate polypeptides, we have observed that it is advantageous to link both proteins covalently. Such covalent linkage is possible by conventional chemical cross-linking procedures; preferably, however, the covalent linkage is achieved by producing a recombinant polypeptide comprising an Aβ peptide and a chaperone.

In a further preferred embodiment, the present invention relates to a process for the production of a soluble Aβ-chaperone complex comprising the steps of solubilizing, under appropriate buffer conditions, a protein comprising a recombinantly linked Aβ and a chaperone protein selected from the peptidyl prolyl isomerase class and thereafter adjusting the buffer to physiological conditions. This way an intramolecular complex is obtained which is soluble to at least 100 nM in a buffer which has a pH of 7.4 and consists of 20 mM sodium phosphate and 150 mM sodium chloride. Most preferred this process is performed starting from so-called inclusion bodies.

In case of the production of an intramolecular complex comprising a PPI-chaperone and Aβ the solubilizing buffer preferably is a buffer with rather a high concentration of a chaotropic salt, e.g., 6.0 M guanidinium chloride at a pH of about 7.8. Upon renaturation the target protein assumes its native-like structure and the intramolecular soluble complex forms.

The present invention teaches the use of chaperones derived from the class of folding helpers termed peptidyl prolyl cis/trans isomerases (PPIs or PPIases) (cf. Dartigalongue, C., and Raina, S., Embo J. 17 (1998) 3968–3980). Well-known examples of this family are members called CypA, PpiD (Dartigalongue, C. and Raina, S., supra; Schmid, F. X., Molecular chaperones in the life cycle of proteins, eds. A. L. Fink and Y. Goto, Marcel Decker Inc., New York (1998), pp. 361–389), FkpA (Danese, P. N., et al., Genes Dev. 9 (1995) 387–398) and trigger factor (Crooke, E., and Wickner, W., Proc. Natl. Acad. Sci. USA 84 (1987) 5216–5220; Stoller, G., et al., Embo J. 14 (1995) 4939–4948).

The peptidyl prolyl isomerases are subdivided into three families, the parvulines (Schmid, F. X., supra; Rahfeld, J. U., et al., FEBS Lett. 352 (1994) 180–184) the cyclophilines (Fischer, G., et al., Nature 337 (1989) 476–478, and the FKBP family (Lane, W. S., et al., J. Protein Chem. 10 (1991) 151–160). The FKBP family exhibits an interesting biochemical feature: its members have originally been identified by their ability to bind to macrolides, e.g., FK 506 and rapamycin (Kay, J. E., Biochem J. 314 (1996) 361–385).

Some prolyl isomerases comprise different subunits or modules of different function, e.g., a module exhibiting catalytic activity and a module exhibiting the chaperone or binding activity. Such modular members of the FKBP family are FkpA (Ramm, K., and Pluckthun, A., J. Biol. Chem. 275 (2000) 17106–17113), SlyD (Hottenrott, S., et al., J. Biol. Chem. 272 (1997) 15697–15701) and trigger factor (Scholz, C., et al., Embo J. 16 (1997) 54–58). Preferably members of the FKBP family of the PPI class of chaperones are used.

In a further embodiment, it is preferred to use homologues derived from eukaryotic organisms, and it is very preferred to use PPIases from human origin because these PPIases should not be recognized by antibodies from human sera and thus should not interfere in serological assays (i.e. assays based on the detection of human antibodies).

It is also well known and appreciated that it is not necessary to always use the complete sequence of a molecular chaperone. Functional fragments of chaperones (so-called modules) which still possess the required abilities and functions may also be used (cf. WO 98/13496).

For instance, FkpA is a periplasmic PPI that is synthesized as an inactive precursor molecule in the bacterial cytosol and translocated across the cytoplasmic membrane. The active form of FkpA (mature FkpA or periplasmic FkpA) lacks the signal sequence (amino acids 1 to 25) and thus comprises amino acids 26 to 270 of the precursor molecule. Relevant sequence information relating to FkpA can easily be obtained from public databases, e.g., from "SWISS-PROT" under accession number P 45523.

A close relative of FkpA, namely SlyD, consists of a structured N-terminal domain responsible for catalytic and chaperone functions and of a largely unstructured C-terminus that is exceptionally rich in histidine and cysteine residues (Hottenrott, S., et al., J. Biol. Chem. 272 (1997) 15697–15701). We found that a C-terminally truncated variant of SlyD comprising amino acids 1–165 efficiently exerts its solubilizing functions on Aβ. Unlike in the wild-type SlyD, the danger of compromising disulfide shuffling is successfully circumvented in the truncated SlyD-variant (1–165) used.

Variants of the above-discussed chaperones, bearing one or several amino acid substitutions or deletions, may also be used to perform a process according to the present invention.

Of course, the present invention is not restricted to the use of the specifically mentioned members of the peptidyl prolyl isomerase class, but can also be performed using chaperones stemming from the same class of chaperones but derived from a different species of bacteria.

Appropriate chaperones from alternative sources, and appropriate fragments or mutants of PPI chaperones, can be easily selected by using the procedures as described in the Examples. Preferred alternative sources for PPI chaperones are *Yersinia pestis, Vibrio cholerae, Pasteurella multocida,* and *Treponema pallidum.*

In a preferred embodiment according to the present invention, a binding-competent PPIase chaperone is recombinantly linked to an Aβ peptide in a way to yield high expression of the gene product in the bacterial cytosol. A binding-competent PPIase as referred to in the present invention encompasses at least the functional unit that mediates binding to extended Aβ peptide substrate (i.e. the substrate binding or chaperone motif), irrespective of its catalytic PPIase activity.

It is known (e.g., Scholz et al., supra) that modular PPIs preferentially bind to denatured or partially denatured proteins. PPIases have now been found to have the striking property of not only catalyzing the folding of proteins, but also of forming stable complexes with such proteins, thereby conferring solubility. Surprisingly the PPIases studied (such as TF, SlyD and FkpA) bind to and thus, e.g., solubilize native-like Aβ peptide.

There is a wealth of information on complex formation between model biomolecules, e.g., between an antibody and an antigen (for review see Braden, B. C., and Poljak, R. J., Faseb J. 9 (1995) 9–16). Usually, complex formation and dissociation occur in parallel; the complex and the binding partners coexist in free equilibrium. Likewise, the same seems true for complexes between PPI chaperones and amyloidogenic proteins, like Aβ, as described in the present invention.

The formation of a complex, as described in the present invention, is an especially important property because a complex between the PPI chaperone and Aβ, a protein that itself is essentially insoluble, has now been found to be readily soluble, e.g., under physiological buffer conditions. Antigens that are soluble under physiological conditions are of tremendous advantage in diagnostic applications. They can be directly used, e.g., as standard material. Furthermore, they can be conjugated to appropriate markers or to appropriate binding groups.

As a typical example for an amyloidogenic peptide the Aβ peptide is extremely difficult to handle and exhibits quite unusual properties. As already mentioned, one of the most critical features of the Aβ molecule is its insolubility at physiological buffer conditions.

Physiological buffer conditions usually are understood to correspond to salt and pH-conditions found in plasma or serum of animals and are defined by a pH value of around 7.4 and a salt concentration of about 150 mM. The Aβ-chaperone complex according to the present invention is readily soluble under these buffer conditions. The Aβ present therein is immunologically active, thus pointing to a native-like structure. Whereas Aβ in the absence of, or without pre-treatment by, an appropriate detergent is essentially insoluble under physiological buffer conditions (e.g., 20 mM sodium phosphate pH 7.4, 150 mM NaCl), the described complex according to this invention is readily soluble after refolding according to the appropriate protocol. The Aβ, as comprised in the inventive complex, is soluble at least at a concentration of 100 nM, preferably at a concentration of 1 μM and above, most preferred at 10 μM or more. Thus, solubility is substantially increased from low nanomolar to about micromolar concentrations.

For a better understanding of the scope of the present invention, it is necessary to emphasize that the buffer conditions applied for solubilization and renaturation may be modified as required and appropriate and must not be understood as an undue restriction of the invention, which is carried out successfully over a broad range of buffer conditions.

The overall salt concentration of the physiological buffer is not critical as long as care is taken that the chaperone-Aβ complex is not dissociated, and Aβ stays in solution. Preferably the physiological buffer comprises at least 10 mM of the buffer system and at most 200 mM. The rest of the buffer constituents, if any, may be a salt without significant buffer capacity, e.g., sodium chloride. The physiological buffer preferably has a salt concentration between 20 and 500 mM, more preferred between 50 and 300 mM, and most preferred between 100 and 200 mM.

In a process according to the present invention, the physiological buffer may be varied to have a pH value in the range of 5.0 to 8.5; more preferred, the range of such buffer is between pH 5.5 and pH 8.3. Even more preferred, such physiological buffer conditions are defined by the salt concentrations as given above and a pH value between 6.0 and 8.0; most preferred, the pH of such physiological buffer is between 6.5 and 7.8.

A preferred embodiment according to the present invention is a process of producing a soluble Aβ-chaperone complex, comprising an Aβ peptide recombinantly linked to a peptidyl prolyl isomerase comprising: solubilizing said recombinant Aβ-chaperone polypeptide, and adjusting the buffer to physiological conditions. Whereas an Aβ peptide alone would spontaneously precipitate when doing so, as part of a recombinant protein according to the present invention it surprisingly stays in solution in the above process. This important finding is most likely due to the formation of an intramolecular complex between Aβ peptide and the chaperone.

In case of the recombinant production of Aβ in *E. coli*, the recombinantly produced Aβ is preferably obtained in the form of inclusion bodies. This material is solubilized using a highly chaotropic reagent, e.g., 7.0 M guanidinium tchloride. The Aβ polypeptide is largely unstructured under these conditions. By changing the buffer in appropriate steps to physiological buffer conditions the Aβ in solution assumes what is perceived as its native like structure. Information on light-straying particles (like aggregates) can easily be obtained from standard UV spectra.

What is important to emphasize here is the fact that the Aβ peptide within the Aβ peptide-chaperone complex, according to the present invention, during transfer to physiological buffer conditions does adopt what is considered to be a native-like fold. On the contrary, Aβ peptide, which has been solubilized at neutral pH by chaotropic agents, is largely unstructured, thus losing ordered conformation epitopes. It is also possible to solubilize an Aβ peptide alternatively by using detergents. For example, sodium dodecyl sulfate (SDS) has successfully been used to solubilize Aβ. However, such "SDS-solubilized material" is not the material of choice, e.g., for use in an immunoassay. Furthermore (as discussed above) such immunoassays preferably make use of antibodies which react with conformational epitopes of Aβ, and it cannot be excluded that detergents do partially abolish conformational epitopes.

Preferably, the Aβ-chaperone complex according to the present invention is characterized in that the Aβ comprised therein is native-like folded. The native-like folded Aβ within such a complex, e.g., exhibits the required immunological or physical features.

Production of the soluble chaperone-Aβ complex starts from non-physiological buffer conditions. The "nonphysiological" buffer has to meet two requirements, that (a) unfolding of Aβ is reversible to its native-like structure, and (b) the unfolding of the PPI-chaperone is reversible to its native-like structure. Starting from such buffer conditions, the chaperone binds to the amyloidogenic target protein, and a change of the buffer conditions from non-physiological to more or less physiological conditions is possible without precipitation of the polypeptide comprising the amyloidogenic Aβ peptide.

Whereas chaperones usually bind to denatured proteins and act upon them, thereby facilitating their correct (re-) folding, the situation on which the present invention is based is strikingly different. Different from the customary view of chaperone functions, in the inventive method the chaperone appears to bind to the native-like folded protein and to stabilize this protein at buffer conditions under which Aβ is otherwise insoluble and aggregates and/or precipitates.

In a preferred embodiment according to the present invention, the PPI chaperone is selected from the group comprising FkpA, SlyD and trigger factor.

It has been found that especially FkpA or SlyD improve the solubility of Aβ and form rather stable complexes therewith. A further preferred embodiment therefore is characterized in that the chaperone is selected from the group comprising FkpA and SlyD. Most preferred the chaperone SlyD is used for conferring solubility to Aβ.

As described further above, also fragments of chaperones may be used to bring about the desired function. In case of the modular chaperones, like the FKBPs, comprising a catalytic module and a binding module, it is preferred that such fragment at least comprises the binding domain, or that such fragment at least exhibits essentially a function comparable to the binding domain. A preferred functional fragment of a PPI-chaperone is for example EcSlyD (1–165) derived from *E. coli*. SlyD homologues corresponding to EcSlyD also represent preferred embodiments according to the pending invention.

FKBP12 is a human member of the FKBP family and essentially comprises the catalytic isomerase domain of a PPIase. Since it lacks an additional polypeptide-binding domain, it displays significantly reduced binding affinity towards unfolded or partially folded protein substrates as compared to other members of the FKBP family. It has been shown that unfolding and refolding of FKBP12 is a reversible process (Egan, D. A., et al., Biochemistry 32 (1993) 1920–1927; Scholz, C., et al., J. Biol. Chem. 271 (1996) 12703–12707). We find that refolding and unfolding of FkpA (25–270) and SlyD (1–165) are reversible either, thus fulfilling a pivotal requisite of the process described here.

A soluble Aβ chaperone complex can also be prepared by mixing the PPI chaperone (e.g., produced by recombinant techniques) and Aβ either obtained by conventional peptide synthesis or produced recombinantly. However, as described above, preferably and quite easily Aβ is obtained in a soluble form by appropriate processing of a recombinant polypeptide comprising a PPI chaperone and Aβ.

In a preferred embodiment, the present invention relates to a complex which is soluble to at least 100 nM in a solution which has a pH of 7.4 and consists of 20 mM sodium phosphate and 150 mM sodium chloride, comprising an Aβ, and a peptidyl prolyl isomerase chaperone, wherein the Aβ and the peptidyl prolyl isomerase chaperone are covalently linked.

Complex formation is a dynamic process in which dissociation and re-association occur in parallel. This is true for both the intermolecular and the intramolecular (e.g., in a fusion construct) association between, e.g., SlyD and Aβ. Since Aβ precipitates from a physiological buffer solution, concentrations of both partners have to be chosen which ensure that only a non-critical or non-aggregating concentration of Aβ in free form is present, and that the vast majority of Aβ is bound and stabilized in form of an Aβ-chaperone complex.

It has been found that a ratio of 1:1 (Aβ to PPI chaperone) is sufficient to form the soluble complex if both domains are covalently linked. Most advantageous molar ratios of Aβ to chaperone are 1:1 and 1:2.

A soluble complex comprising an Aβ peptide and a PPI chaperone in a recombinantly linked form represents a very preferred embodiment according to the present invention. Most preferred an Aβ peptide comprised in such a recombinant polypeptide is selected from the group consisting of Aβ(1–40), Aβ(1–42), and Aβ(1–43).

For a recombinant protein comprising at least one Aβ domain and at least one PPI-chaperone domain the transfer from non-physiological to physiological buffer conditions can be accomplished in different ways. Soluble intramolecular complexes between the Aβ domain and, e.g., the SlyD domain are easily obtained by adjusting the non-physiological buffer conditions to physiological buffer conditions by dialysis, rapid dilution or matrix-assisted refolding. Matrix-assisted re-folding representing a preferred method. The solution thus obtained, comprising the soluble Aβ-chaperone complex can be directly used for further modification.

Preferably the recombinant polypeptide according to the present invention comprises one Aβ domain per one chaperone domain. In yet a further preferred embodiment the present invention relates to a recombinant protein comprising at least one Aβ domain and at least two PPI-chaperone domains. Recombinant polypeptides comprising one Aβ domain and two PPI-chaperones are also preferred.

The recombinant polypeptide used to obtain a soluble Aβ chaperone complex according to the present invention is expressed, by means of standard molecular biology techniques. Preferably the chaperone gene is placed in frame upstream the target protein gene into an expression vector comprising both the genetic information for Aβ and the chaperone and optionally also the genetic information for an appropriate peptidic linker sequence. A preferred host for large-scale production of such a recombinant fusion protein is *E. coli*.

In a preferred embodiment, the present invention relates to a soluble complex comprising an Aβ and a chaperone selected from the peptidyl prolyl isomerase class of chaperones. Most preferred the PPI chaperone part of the recombinant polypeptide lacks any export signal peptide (of the corresponding precursor molecule) and corresponds to the mature PPI chaperone. Since in this preferred embodiment the recombinant protein lacks a functional signal sequence, the gene product accumulates in the bacterial cytosol.

A striking feature of Aβ comprised, e.g., in a recombinantly produced SlyD-Aβ is its exceptional solubility as compared to the "unchaperoned" Aβ. It is interesting that the "chaotropic material" (i.e. SlyD-Aβ in 6.0–7.0 M GuHCl) can be refolded in different ways, all resulting in a thermodynamically stable and soluble native-like form. Refolding is achieved at high yields, both by dialysis and by rapid dilution, as well as by renaturing size exclusion chromatography or matrix-assisted refolding. These findings suggest that in this covalently linked form, the Aβ-SlyD fusion polypeptide is a thermodynamically stable rather than a metastable protein.

The recombinant SlyD-Aβ polypeptide comprises two protein domains having different folding requirements. Since the purification protocol includes an initial denaturation step, it is mandatory that the folding of the chaperone be reversible. Indeed, there is compelling spectroscopic evidence for the reversible unfolding and refolding of both SlyD and Aβ within the covalently linked protein complex.

Also preferred is a recombinant polypeptide which is soluble to at least 100 nM in a solution which has a pH of 7.4 and consists of 20 mM sodium phosphate and 150 mM sodium chloride, comprising an Aβ, a peptidic linker, and a peptidyl prolyl isomerase chaperone.

The peptide linker sequence of such recombinant polypeptide is selected to ensure optimal intramolecular association of the Aβ and the chaperone domain used. Preferably, such a linker sequence is about 20 amino acids long and comprises amino acids supporting both flexibility and solubility, such as e.g., glycine and serine. Preferably the linker is 10 to 50 amino acids in length. More preferred the length is 12 to 40 amino acids, and most preferred, the linker comprises 15 to 35 amino acids. Both the Aβ and the chaperone are always in close proximity (held together, e.g., by an appropriate linker). In a preferred embodiment the recombinant polypeptide comprises mature FkpA or truncated SlyD (amino acids 1–165) linked to its target protein via a flexible linker. This, as the data indicate, brings about an additional stabilizing effect.

It has surprisingly been found that Aβ, as part of the intramolecular complex between a PPI chaperone and Aβ, is both soluble and stable. The improved stability of Aβ in such a complex brings about additional advantages. For example, it is possible to obtain a fully re-natured recombinant Aβ-chaperone molecule very easily. The recombinant protein is initially solubilized by treatment with a chaotropic agent (e.g., guanidinium chloride). By simply passing the solubilized material over a gel filtration column, equilibrated with the appropriate physiological buffer, a fully re-natured protein comprising the covalently linked protein domains can be obtained.

Matrix-assisted refolding can also be easily and to great advantage applied, see Example 2 and FIG. 2. There it is shown that in a very convenient renaturation and easy purification step a soluble SlyD-SlyD-Aβ fusion protein is obtained with a purity of about 90%.

It is a very important feature of the complex, according to the present invention, that Aβ within such complex Aβ is present in a soluble form under physiological buffer conditions, e.g., at pH 7.4 in 20 mM phosphate 150 mM sodium chloride buffer. Unlike free Aβ the Aβ comprised in such complex is neither sticky nor aggregation prone. This is a tremendous advantage for therapeutic as well as for diagnostic applications. In a preferred embodiment, the present invention relates to a composition of reagents that is soluble under physiological buffer conditions, comprising an intramolecular complex comprising an Aβ peptide and a chaperone selected from the peptidyl prolyl isomerase class of chaperones.

A soluble complex comprising native-like folded Aβ and a chaperone selected from the peptidyl prolyl isomerase class of chaperones represents a very preferred embodiment of the present invention.

In terms of immunization with Aβ, the progress made by providing a "soluble and native-like" Aβ is quite obvious. For the first time soluble and native-like Aβ is now available for injection under physiological buffer conditions.

In a preferred embodiment, the soluble complex as described is used to produce a composition of reagents for use as a medicament. The composition of reagents comprises the Aβ-chaperone complex together with physiologically acceptable excipients and, where appropriate, suitable additives and/or conventional auxiliary substances.

It represents a further preferred embodiment according to the present invention to form a composition of reagents comprising an Aβ-chaperone complex and to use such a composition for eliciting an immune response in a mammal. The complex described makes available much more Aβ epitopes than any other Aβ immunogen known. The novel immunogen therefore is expected to induce a much broader immune response.

With respect to diagnostic procedures, obvious advantages of a soluble Aβ-chaperone complex according to the present invention are, e.g., the increased stability of a Aβ peptide, under physiological buffer conditions, and/or the increase in diagnostic sensitivity, and/or the increased numbers of conformational epitopes present, and/or the possibility to easily label the Aβ-chaperone complex.

In terms of labeling the mode and strategy of chemical coupling can now be selected as required. In case of polypeptides, coupling chemistries targeting —SH, —NH$_2$ or —COO residues as well as the —OH group of tyrosine, the imidazol group of histidine, or the heterocyclic imino groups of tryptophane are at hand. Several appropriate coupling chemistries are known for each of these functional groups (Aslam, M. and Dent, A., supra). Routine protein coupling chemistries require a protein to be soluble under the working buffer conditions, e.g., within a pH range of about 5 to 8.5.

Well-known labels are marker groups or effector groups, like solid phase binding groups. A labeled soluble Aβ-chaperone complex represents a further preferred embodiment according to the present invention.

The labeling group can be selected from any known detectable marker groups, such as dyes, luminescent labeling groups such as chemiluminescent groups, e.g., acridinium esters or dioxetanes, or fluorescent dyes, e.g., fluorescein, coumarin, rhodamine, oxazine, resorufin, cyanine and derivatives thereof. Other examples of labeling groups are luminescent metal complexes, such as ruthenium or europium complexes, enzymes, e.g., as used for ELISA or for CEDIA (Cloned Enzyme Donor Immunoassay, e.g., EP-A-0 061 888), and radioisotopes.

Effector groups comprise, for example, one partner of a bioaffine binding pair. While performing an assay, the effector group interacts specifically and preferably non-covalently with the other partner of the bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred binding pair members comprise hapten, antigen and hormone. Especially preferred are haptens like digoxin and biotin and analogues thereof.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: "Practice and theory of enzyme immunoassays", eds. R. H. Burdon and v. P. H.

Knippenberg, Elsevier, Amsterdam (1990), pp. 221–278) and various volumes "Methods in Enzymology", eds. S. P. Colowick, N. O. Caplan, Academic Press (1980)), dealing with immunological detection methods, especially volumes 70, 73, 74, 84, 92 and 121.

The present invention relates to the use of a soluble chaperone-Aβ complex in an immunoassay. The soluble complex comprising Aβ and a PPI chaperone is preferably used as a standard material in an immunoassay for detection of the Aβ peptide. In a further preferred embodiment, a labeled soluble complex comprising Aβ and a PPI chaperone is used in an immunoassay for detection of antibodies to Aβ.

The novel chaperone-Aβ complex provides for the possibility to derivatise the chaperone of such a complex and does not require the modification of the antigen (Aβ) itself. It is generally accepted that the modification of a polypeptide by a second chemical moiety, for example, the coupling of a label to that molecule, includes the risk of negatively influencing the polypeptide. For example, the epitope under investigation may be compromised, or such labeling may cause non-specific binding. According to the present invention, it is now possible to derivatise specifically the chaperone within a chaperone-Aβ complex.

Diagnostic reagents in the field of specific binding assays, like immunoassays, usually are best provided in the form of a kit, which comprises the specific binding agent or agents and the auxiliary reagents required to perform the assay. The present invention therefore also relates to an immunological kit comprising at least one composition of reagents comprising an Aβ-chaperone complex according to the present invention and auxiliary reagents for performing an Aβ measurement. Preferably the composition of reagents comprising the Aβ-chaperone complex is provided in liquid form.

In another embodiment, a soluble complex comprising Aβ and a PPI chaperon may also be used to elicit an immune response in a subject, such as a human or non-human animal. The soluble complexes may be administered to a subject in compositions, such as those that may contain an excipient or carrier. Such compositions may also include an adjuvant. Examples of conventional adjuvants include, but are not limited to, Freund's incomplete, Freund's complete, Merck 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol. Other useful adjuvants include, but are not limited to, bacterial capsular polysaccharides, dextran, IL-12, GM-CSF, CD40 ligand, IFN-γ, IL-1, IL-2, IL-3, IL-4, IL-10, IL-13, IL-18 or any cytokine or bacterial DNA fragment.

One dose (administration) of a soluble complex composition may be given. However, boosting doses, such as once, twice, three times or more may follow the first administration. The number of doses administered to a subject depends on in part by the response of a subject to a soluble complex composition. Within the scope of the present invention, a suitable number of doses include any number required to immunize an animal to soluble complex.

A second administration (booster) of the soluble complex composition may be given between about 7 days and 1 year after the first administration. The time between the first and second administrations may be 14 days to 6 months, 21 days and 3 months, often between about 28 days and 2 months after the original administration. A third administration (second booster) may be given between about 14 days and 10 years after the first administration, e.g., between about 14 days and 3 years, often between about 21 days and 1 year, very often between about 28 days and 6 months after the first administration. Subsequent boosters may be administered at 2 week intervals, or 1 month, 3 month or 6 month to 10 year intervals.

Typically, the amount of soluble complex will be administered to a subject that is sufficient to immunize an animal against an antigen (i.e., an "immunologically effective dose" or a "therapeutically effective dose"). An amount adequate to accomplish an "immunologically effective dose" will depend in part on the weight and general state of health of the subject, and the judgment of the prescribing physician or other qualified personnel.

The effective dose of the soluble complex can be formulated in animal models to achieve an induction of an immune response; such data can be used to readily optimize administration to humans based on animal data. A dose will typically be between about 1 μg and about 100 μg, often between about 1 μg and about 100 μg, more often between about 1 ng and about 50 μg, and usually between about 100 ng and about 50 μg. In some embodiments, the dose is between about 1μ and about 100 μg per kg subject body weight, often between about 1μ and about 100 μg, more often between about 1 ng and about 50μ, and usually between about 100 ng and about 50 μg per kg subject body weight.

The soluble complex-containing compositions of the invention may be administered in a variety of ways and in various forms. A soluble complex composition may include carriers and excipients, such as buffers, carbohydrates, mannitol, proteins, polypeptides or amino acids such as glycine, antioxidants, bacteriostats, chelating agents, suspending agents, thickening agents and/or preservatives; water, oils, saline solutions, aqueous dextrose and glycerol solutions, other pharmaceutically acceptable auxiliary substances as required to approximate physiological conditions, such as buffering agents, tonicity adjusting agents, wetting agents, etc. A conventional adjuvant may also be incorporated into the composition.

While any suitable carrier may be used to administer the compositions of the invention, the type of carrier will vary depending on the mode of administration. Compounds may also be encapsulated within liposomes. Biodegradable microspheres are convenient in some instances as carriers; for example, such as those described in U.S. Pat. No. 5,942,252.

Sterilization of the compositions is desirable, such as that accomplished by conventional techniques, such as sterile filtering. The resulting aqueous solutions may be packaged for use as is, or lyophilized.

The soluble complex compositions of the invention may be administered in a variety of ways, including by injection (e.g., intradermal, subcutaneous, intramuscular, intraperitoneal etc.), by inhalation, by topical administration, by suppository, by using a transdermal patch or by mouth.

When administration is by injection, compositions may be formulated in aqueous solutions, preferably in physiologically compatible buffers such as Hanks solution, Ringer's solution, 20 mM phosphate 150 mM sodium chloride buffer (pH7.4), or physiological saline buffer. The solution may contain formulator agents such as suspending, stabilizing and/or dispersing agents. Alternatively, the composition may be in powder form for constitution with a suitable vehicle, e.g., sterile pyrogen-free water, before use. Inhalation-delivered compositions may be as aerosol sprays from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch. For topical administration, the compositions may be formulated as solutions, gels, ointments, creams, suspensions, and the like, as are well known in the art. In some embodiments, administration is by means of a transdermal patch. Suppository compositions may also be formulated to contain conventional suppository bases.

When administration is oral, a composition can be readily formulated by combining the composition with pharmaceutically acceptable carriers. Solid carriers include mannitol, lactose, magnesium stearate, etc.; such carriers enable the formation of tablets, pills, dragees, capsules, liquids, gels, syrups, slurries, suspensions etc., for oral ingestion. Such formulations may be powders, capsules and tablets; suitable excipients include fillers such as sugars, cellulose preparation, granulating agents, and binding agents.

Methods of producing polyclonal and monoclonal antibodies, including binding fragments (e.g., F(ab)2) and single chain versions are well known. However, many antigens are incapable of triggering an adequate antibody response. In one embodiment, a composition comprising a soluble complex of the invention and an antigen is administered to an animal, thus eliciting an immune response in the animal. Polyclonal or monoclonal antibodies are subsequently prepared by standard techniques.

The following examples, references, sequence listing and figures are provided to aid the understanding of the present invention, the true scope of which is set forth in the appended claims. It is understood that modifications can be made in the procedures set forth without departing from the spirit of the invention.

EXAMPLES

Example 1

Construction of an SS-Aβ(1–42) expression vector

The gene encoding the chaperone SlyD has been isolated by routine cloning procedures from the chromosome of *E. coli* (Ec). For recombinant expression a DNA construct has been prepared coding for amino acids 1 to 165 of SlyD (=EcSlyD). An expression vector has been constructed comprising twice EcSlyD(1–165) (=SS) as fusion partner and Aβ(1–42) as target protein.

On the basis of the pET24a expression plasmid of Novagen (Madison, Wis., USA) the following cloning steps were performed. The vector was digested with NdeI and XhoI and a semi-synthetic cassette comprising tandem-EcSlyD and Aβ(1–42) was inserted:

| Nde I | | | | BamH I | | Xho |
|---|---|---|---|---|---|---|
| EcSlyD | L | EcSlyD | L | Aβ(1–42) | | |

L = (GGGS)$_5$GGG-Linker

The insert of the resulting plasmid was sequenced and found to encode the desired fusion protein.

The nucleic acid sequence of the inserted cassette (=SEQ ID NO:1) is given below.

```
CATATGAAAGTAGCAAAAGACCTGGTGGTCAGCCTGGCCTATCAGGTA
CGTACAGAAGACGGTGTGTTGGTTGATGAGTCTCCGGTGAGTGCGCCGC
TGGACTACCTGCATGGTCACGGTTCCCTGATCTCTGGCCTGGAAACGGC
GCTGGAAGGTCATGAAGTTGGCGACAAATTTGATGTCGCTGTTGGCGCG
AACGACGCTTACGGTCAGTACGACGAAAACCTGGTGCAACGTGTTCCT
AAAGACGTATTTATGGGCGTTGATGAACTGCAGGTAGGTATGCGTTTCC
TGGCTGAAACCGACCAGGGTCCGGTACCGGTTGAAATCACTGCGGTTG
AAGACGATCACGTCGTGGTTGATGGTAACCACATGCTGGCCGGTCAGA
ACCTGAAATTCAACGTTGAAGTTGTGGCGATTCGCGAAGCGACTGAAG
AAGAACTGGCTCATGGTCACGTTCACGGCGCGCACGATCACCACCACG
ATCACGACCACGACGGTGGCGGTTCCGGCGGTGGCTCTGGTGGCGGAA
GCGGTGGCGGTTCCGGCGGTGGCTCTGGTGGCGGTAAAGTAGCAAAAG
ACCTGGTGGTCAGCCTGGCCTATCAGGTACGTACAGAAGACGGTGTGTT
GGTTGATGAGTCTCCGGTGAGTGCGCCGCTGGACTACCTGCATGGTCAC
GGTTCCCTGATCTCTGGCCTGGAAACGGCGCTGGAAGGTCATGAAGTTG
GCGACAAATTTGATGTCGCTGTTGGCGCGAACGACGCTTACGGTCAGTA
CGACGAAAACCTGGTGCAACGTGTTCCTAAAGACGTATTTATGGGCGTT
GATGAACTGCAGGTAGGTATGCGTTTCCTGGCTGAAACCGACCAGGGT
CCGGTACCGGTTGAAATCACTGCGGTTGAAGACGATCACGTCGTGGTTG
ATGGTAACCACATGCTGGCCGGTCAGAACCTGAAATTCAACGTTGAAG
TTGTGGCGATTCGCGAAGCGACTGAAGAAGAACTGGCTCATGGTCACG
TTCACGGCGCGCACGATCACCACCACGATCACGACCACGACGGTGGCG
GTTCCGGCGGTGGCTCTGGTGGCGGATCCGGTGGCGGTTCCGGCGGTGG
CTCTGGTGGCGGTGACGCTGAATTCCGTCACGACTCCGGTTACGAAGTT
CACCACCAGAAACTGGTTTTCTTCGCTGAAGACGTTGGTTCCAACAAAG
GTGCTATCATCGGTCTGATGGTTGGTGGTGTTGTTATCGCTCTCGAGCA
CCACCACCACCACTGA
```

The amino acid sequence of the resulting fusion polypeptide is given below (=SEQ ID NO:2):

1 MKVAKDLVVS LAYQVRTEDG VLVDESPVSA PLDYLHGHGS LISGLETALE
51 GHEVGDKFDV AVGANDAYGQ YDENLVQRVP KDVFMGVDEL QVGMRFLAET
101 DQGPVPVEIT AVEDDHVVVD GNHMLAGQNL KFNVEVVAIR EATEEELAHG
151 HVHGAHDHHH DHDHDGGGSG GGSGGGSGGG SGGGSGGGKV AKDLVVSLAY
201 QVRTEDGVLV DESPVSAPLD YLHGHGSLIS GLE- TALEGHE VGDKFDVAVG
251 ANDAYGQYDE NLVQRVPKDV FMGVDELQVG MRFLAETDQG PVPVEITAVE
301 DDHVVVDGNH MLAGQNLKFN VEVVAIREAT EEELAHGHVH GAHDHHHDHD
351 HDGGGSGGGS GGGSGGGSGG GSGGGDAEFR HDSGYEVHHQ KLVFFAEDVG
401 SNKGAIIGLM VGGVVIALEH HHHHH

Example 2

Production and Purification of the SS-Aβ(1–42) Fusion Protein

*E. coli* BL21(DE3) cells harboring the expression plasmid were grown in LB medium plus kanamycin to an OD600

(optical density at 600 nm) of 1, and cytosolic overexpression was induced by adding isopropyl-β-D-thiogalactoside (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 50 mM Tris/HCl pH 8.5, 7.0 M GuHCl, 5 mM imidazole at room temperature and the resulting suspension was further subjected to treatment with a Polytronic® PT 3100 homogenizer (Kinematica). After centrifugation (20000×g, 4° C., 30 min) and filtration, the lysate was applied onto a Ni-NTA (nickel-nitrilo-triacetate) column pre-equilibrated in the aforementioned lysis buffer.

After an excessive washing step (>20 column volumes of lysis buffer), the chaotropic lysis buffer was displaced by 50 mM sodium phosphate pH 7.8, 100 mM sodium chloride in order to allow the matrix bound protein to refold. At least 10 column volumes of refolding buffer were applied to make sure there was no GuHCl in a chaotropic or interfering concentration left. Finally, the native fusion protein was eluted by applying an imidazole gradient from 5–500 mM in 50 mM sodium phosphate pH 7.8, 100 mM sodium chloride. Protein containing fractions were assessed for purity by sodium dodecylsulfate polyacrylamide gel electrophoresis (SDS-PAGE) and pooled.

Figure 1:
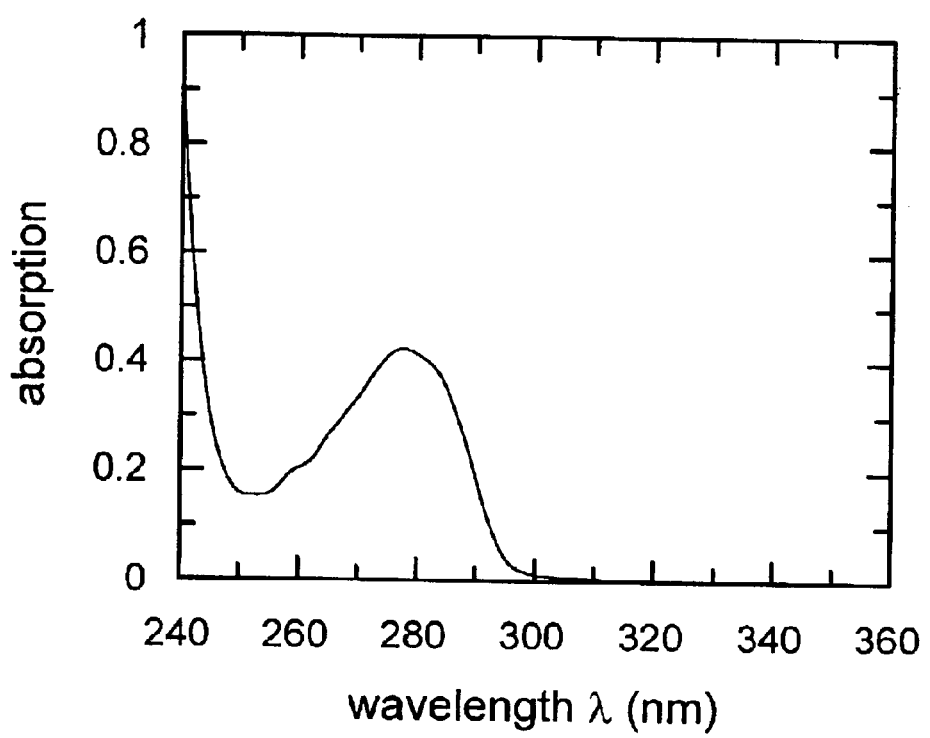
FIG. 1: UV-spectrum of SS-Aβ(1-42) after matrix-assisted refolding and gradient elution.

Intriguingly, SS-Aβ(1–42) elutes as a soluble protein. Despite the notorious hydrophobicity of the Aβ(1–42) itself, the UV spectrum of the recombinantly produced and matrix-refolded fusion protein does not indicate any aggregation tendency. As shown in FIG. 1, the baseline of the UV-absorption spectrum of SS-Aβ in physiological buffer conditions almost equals the abscissa (beyond 310 nm), thus indicating that there are no light-straying particles resulting from self-association or aggregation phenomena. Indeed, the shape of the spectrum depicted in FIG. 1 points to a soluble, easy-to-handle fusion polypeptide comprising the Aβ (1–42) peptide that should prove useful as a diagnostic tool (e.g. as a standard for an Aβ immunoassay) or as an immunogen.

In short, the method described here facilitates the convenient recombinant production of a Aβ in a soluble form and in high amounts (yield >20 mg fusion protein/g wet weight of E. coli cell mass).

The fusion protein SS-Aβ(142) elutes at about 150 mM imidazole from the Ni-NTA column. Purity of the pooled fractions containing the fusion protein was assessed by sodium dodecyl sulfate polyacrylamide gel electrophoresis (SDS-PAGE). As shown by SDS-PAGE the purity of the fusion polypeptide as obtained in a single combined purification and renaturation step exceeds 90% after a simple one-step chromatography protocol (cf. FIG. 2).

LIST OF REFERENCES

Aslam, M. and Dent, A., The preparation of protein—protein conjugates in "Bioconjugation", eds. M. Aslam and A. Dent, McMillan Reference, London (1998), pp. 216–363
Braden, B. C., and Poljak, R. J., Faseb J. 9 (1995) 9–16
Crooke, E., and Wickner, W., Proc. Natl. Acad. Sci. USA 84 (1987) 5216–5220
Danese, P. N., et al., Genes Dev. 9 (1995) 387–398
Dartigalongue, C., and Raina, S., Embo J. 17 (1998) 3968–3980
Egan, D. A., et al., Biochemistry 32 (1993) 1920–1927
EP-A-0 061 888
Fischer, G., et al., Nature 337 (1989) 476–478
Glenner, G. G., and Wong, C. W., Biochem. Biophys. Res. Commun. 120 (1984) 885–890
Glenner, G. G., and Wong, C. W., Biochem. Biophys. Res. Commun. 122 (1984) 1131–1135
Hottenrott, S., et al., J. Biol. Chem. 272 (1997) 15697–15701
Iwatsubo, T., et al., Neuron 13 (1994) 45–53
Kang, J., et al., Nature 325 (1987) 733–736
Kay, J. E., Biochem J. 314 (1996) 361–385
Lane, W. S., et al., J. Protein Chem. 10 (1991) 151–160
Masters, C. L., et al., Proc. Natl. Acad. Sci. USA 82 (1985) 4245–4249
Rahfeld, J. U., et al., FEBS Lett. 352 (1994) 180–184
Ramm, K., and Pluckthun, A., J. Biol. Chem. 275 (2000) 17106–17113
Roher, A. E., et al., Proc. Natl. Acad. Sci. USA 90 (1993) 10836–10840
Schmid, F. X., Molecular chaperones in the life cyle of proteins, eds. A. L. Fink and Y. Goto, Marcel Decker Inc., New York (1998), pp. 361–389
Scholz, C., et al., Embo J. 16 (1997) 54–58
Scholz, C., et al., J. Biol. Chem. 271 (1996) 12703–12707
Selkoe, D. J., et al., J. Neurochem. 46 (1986) 1820–1834
Selkoe, D. J., J. Neuropath, and Exp. Neurol. 53 (1994) 438–447
Selkoe, D. J., Neuron 6 (1991) 487
Stoller, G., et al., Embo J. 14 (1995) 4939–4948
SWISS-PROT, accession number P 45523
Tijssen, In: "Methods in Enzymology", eds. S. P. Colowick, N. O. Caplan, Academic Press (1980)
Tijssen, P., Preparation of enzyme-antibody or other enzyme-macromolecule conjugates, In: "Practice and theory of enzyme immunoassays", eds. R. H. Burdon and v. P. H. Knippenberg, Elsevier, Amsterdam (1990), pp. 221–278
U.S. Pat. No. 5,942,252
WO 98/13496

We claim:

1. A protein which is soluble to at least 100 nM in a solution which has a pH of 7.4 and consists of 20 nM sodium phosphate and 150 nM sodium chloride, said protein comprising:
   an amyloid β(Aβ) peptide, and
   a peptidyl prolyl isomerase chaperone,
wherein the PrP and the peptidyl prolyl isomerase chaperone are covalently linked.

2. The protein of claim 1, wherein the Aβ peptide and the peptidyl prolyl isomerase chaperone are linked recombinantly.

3. The protein of claim 1, wherein the protein is soluble to at least 1 µM.

4. The protein of claim 1, wherein the protein is soluble to at least 10 µM.

5. The protein of claim 1, wherein the Aβ peptide is selected from the group consisting of Aβ(1–40), Aβ(1–42), and Aβ(1–43).

6. The protein of claim 1, wherein the peptidyl prolyl isomerase chaperone is an FKBP chaperone.

7. The protein of claim 6, wherein the FKBP chaperone is selected from the group consisting of SlyD, FkpA, and trigger factor.

8. The protein of claim 1, wherein the ratio of Aβ peptide to peptidyl prolyl isomerase chaperone is 1:1.

9. The protein of claim 1, wherein the ratio of Aβ peptide to peptidyl prolyl isomerase chaperone is 1:2.

10. The protein of claim 1, said protein further comprising a label.

11. An immunoassay reagent for the detection of antibodies against Aβ peptide comprising the protein of claim 1.

12. A recombinant polypeptide which is soluble to at least 100 nM in a solution which has a pH of 7.4 and consists of 20 nM sodium phosphate and 150 nM sodium chloride, said recombinant polypeptide comprising:
    an amyloid β(Aβ) peptide,
    a peptidic linker, and
    a peptidyl prolyl isomerase chaperone.

13. The recombinant polypeptide of claim 12, wherein the protein is soluble to at least 1 µM.

14. The recombinant polypeptide of claim 12, wherein the protein is soluble to at least 10 µM.

15. The recombinant polypeptide of claim 12, wherein the Aβ peptide is selected from the group consisting of Aβ(1–40), Aβ(1–42), and Aβ(1–43).

16. The recombinant polypeptide of claim 12, wherein the peptidyl prolyl isomerase chaperone is an FKBP chaperone.

17. The recombinant polypeptide of claim 16, wherein the FKBP chaperone is selected from the group consisting of SlyD, FkpA, and trigger factor.

18. The recombinant polypeptide of claim 17, wherein the FKBP chaperone is selected from the group consisting of FkpA and truncated SlyD.

19. The recombinant polypeptide of claim 12, wherein the peptidic linker comprises at least 20 amino acids.

20. The recombinant polypeptide of claim 12, wherein the peptidic linker is 10 to 50 amino acids in length.

21. The recombinant polypeptide of claim 12, wherein the peptidic linker is 15 to 35 amino acids in length.

22. The recombinant polypeptide of claim 12, wherein the ratio of Aβ peptide to peptidyl prolyl isomerase chaperone is 1:1.

23. The recombinant polypeptide of claim 12, wherein ratio of Aβ peptide to peptidyl prolyl isomerase chaperone is 1:2.

24. The recombinant polypeptide of claim 12, said protein further comprising a label.

25. An immunoassay reagent for the detection of antibodies against Aβ peptide comprising the recombinant polypeptide of claim 12.

26. A recombinantly-produced fusion polypeptide comprising:
   an amyloid β(Aβ) peptide, and
   an FKBP chaperone polypeptide, wherein said FKBP chaperone polypeptide is selected from the group consisting of FkpA, SlyD, and trigger factor.

27. The fusion polypeptide of claim 26, wherein the Aβ peptide is selected from the group consisting of Aβ(1–40), Aβ(1–42), and Aβ(1–43).

28. An expression vector comprising:
   at least one nucleic acid sequence encoding an amyloid β(Aβ) peptide,
   at least one nucleic acid sequence encoding a peptidic linker, and
   at least one nucleic acid sequence encoding an FKBP chaperone selected from the group consisting of FkpA, SlyD, and trigger factor.

29. The expression vector of claim 28, wherein the nucleic acid sequence encoding an FKBP chaperone is placed into said expression vector upstream of the nucleic acid sequence encoding the peptidic linker and the nucleic acid sequence encoding Aβ peptide.

30. A method for eliciting an immune response in a subject comprising administering a composition comprising the protein of claim 1 to said subject, thereby eliciting antibodies in said subject, said antibodies having the ability to bind the Aβ peptide.

31. The method of claim 30, wherein the Aβ peptide is selected from the group consisting of Aβ(1–40), Aβ(1–42), and Aβ(1–43).

32. A method for producing antibodies to an Aβ peptide comprising administering the protein of claim 1 to an animal, thus eliciting an immune response in the animal, and isolating antibodies having the ability to bind the Aβ peptide.

33. The method of claim 32, wherein the antibody to the Aβ peptide is a monoclonal antibody.

34. The method of claim 32, wherein the antibody to the Aβ peptide is a polyclonal antibody.

35. A method for eliciting an immune response in a subject comprising administering a composition comprising the recombinant polypeptide of claim 12, to said subject, thereby eliciting antibodies in said subject, said antibodies having the ability to bind the Aβ peptide.

36. The method of claim 35, wherein the Aβ peptide is selected from the group consisting of Aβ(1–40), Aβ(1–42), and Aβ(1–43).

37. A method for producing antibodies to an Aβ peptide comprising administering the recombinant polypeptide of claim 12, to an animal, thus eliciting an immune response in the animal, and isolating antibodies having the ability to bind the Aβ peptide.

38. The method of claim 37, wherein the antibody to the Aβ peptide is a monoclonal antibody.

39. The method of claim 37, wherein the antibody to the Aβ peptide is a polyclonal antibody.

40. A method for producing a soluble amyloid β(Aβ) peptide-chaperone protein comprising:
   incubating a protein comprising Aβ peptide covalently linked to a peptidyl prolyl isomerase chaperone in a nonphysiological buffer wherein both the Aβ peptide and the chaperone are solubilized, and
   adjusting the buffer to physiological conditions wherein the Aβ-chaperone protein formed is soluble to at least 100 nM, said buffer at physiological conditions comprising a pH of 7.4, 20 mM sodium phosphate, and 150 mM sodium chloride.

41. The method of claim 40, wherein the Aβ peptide and the peptidyl prolyl isomerase chaperone are linked recombinantly.

42. The method of claim 41, wherein the peptidyl prolyl isomerase chaperone is an FKBP chaperone.

43. The method of claim 40, wherein the Aβ peptide is selected from the group consisting of Aβ(1–40), Aβ(1–42), and Aβ(1–43).

44. The method of claim 40, wherein the peptidyl prolyl isomerase chaperone is an FKBP chaperone.

45. The method of claim 44, wherein the FKBP chaperone is selected from the group consisting of FkpA, SlyD, and trigger factor.

46. The method of claim 45, wherein the SlyD chaperone is an EcSlyD chaperone derived from *E. coli*.

47. The method of claim 40, wherein the Aβ peptide is produced recombinantly.

48. The method of claim 40, wherein the peptidyl prolyl isomerase chaperone is produced recombinantly.

49. The method of claim 40, wherein the peptidyl prolyl isomerase chaperone is of human origin.

50. The method of claim 40, wherein the peptidyl prolyl isomerase chaperone is derived from an organism selected from the group consisting of *Yersinia pestis*, *Vibrio cholerae*, *Pasteurella multocida*, and *Treponema pallidum*.

51. The method of claim 40, wherein the peptidyl prolyl isomerase chaperone is a binding-competent fragment of the peptidyl prolyl isomerase chaperone.

52. The method of claim 40, wherein the polypeptide is solubilized with a chaotropic reagent.

53. The method of claim 52, wherein the chaotropic agent is 7.0 M guanidinium chloride.

* * * * *

UNITED STATES PATENT AND TRADEMARK OFFICE
CERTIFICATE OF CORRECTION

PATENT NO. : 7,094,884 B2
APPLICATION NO. : 10/443654
DATED : August 22, 2006
INVENTOR(S) : Christian Scholz et al.

It is certified that error appears in the above-identified patent and that said Letters Patent is hereby corrected as shown below:

On the Title Page

In column 1, item (54), and Col. 1 line 1 after "SOLUBLE COMPLEXES OF" delete "AMYLOD" and substitute --AMYLOID-- in its place.

In column 2, line 36, under "OTHER PUBLICATIONS", before "*Membrane Proteins*" delete "*Other*" and substitute --*Outer*-- in its place.

In column 2, line 40, after "Chapter 5, pp. 261-" delete "263" and substitute --363-- in its place.

Page 2, in column 1, line 19, under "OTHER PUBLICATIONS", before "Life Sciences" delete "Molecullar" and substitute --Molecular-- in its place.

Page 2, in column 1, line 25, under "OTHER PUBLICATIONS", before "*-Regulate Peptidyl*" delete "*al-Ion*" and substitute --*al Ion*-- in its place.

Page 2, in column 1, line 41, under "OTHER PUBLICATIONS", after "*A Trimeric*" delete "*Structured*" and substitute --*Structural*-- in its place.

Page 2, in column 1, line 47, under "OTHER PUBLICATIONS", after "*of Simian*" delete "*Immunodificiency*" and substitute --*Immunodeficiency*-- in its place.

Page 2, in column 2, line 9, delete "13363-1383" and substitute --13363-13383-- in its place.

Page 2, in column 2, lines 30-31, after "*Protein-Like*" delete "*Molecular*" and substitute --*Molecule*-- in its place.

Page 2, in column 2, line 36, after "*Enzyme-Antibody*" delete "*of*" and substitute --*or*-- in its place.

In the Claims

Columns 25, in claim 35, line 67, immediately after "claim 12" delete "," (comma).

UNITED STATES PATENT AND TRADEMARK OFFICE
CERTIFICATE OF CORRECTION

PATENT NO. : 7,094,884 B2
APPLICATION NO. : 10/443654
DATED : August 22, 2006
INVENTOR(S) : Christian Scholz et al.

It is certified that error appears in the above-identified patent and that said Letters Patent is hereby corrected as shown below:

In the Claims (cont'd)

Column 26, in claim 37, line 8, immediately after "claim 12" delete "," (comma).

Column 26, in claim 40, lines 22-23, after "physiological conditions" start a new paragraph with "wherein the Aβ-chaperone protein formed".

Signed and Sealed this

Third Day of April, 2007

JON W. DUDAS
*Director of the United States Patent and Trademark Office*